United States Patent
Cahan

(10) Patent No.: US 9,668,992 B1
(45) Date of Patent: *Jun. 6, 2017

(54) SCFA COLONIC COMPOSITION

(71) Applicant: INTERNATIONAL BUSINESS MACHINES CORPORATION, Armonk, NY (US)

(72) Inventor: Amos Cahan, Dobbs Ferry, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,611

(22) Filed: Jun. 2, 2016

Related U.S. Application Data

(62) Division of application No. 14/963,521, filed on Dec. 9, 2015.

(51) Int. Cl.
- *A61K 31/19* (2006.01)
- *A61K 47/38* (2006.01)
- *A61K 47/32* (2006.01)

(52) U.S. Cl.
CPC .............. *A61K 31/19* (2013.01); *A61K 47/32* (2013.01); *A61K 47/38* (2013.01)

(58) Field of Classification Search
CPC ......... A61K 31/19; A61K 47/38; A61K 47/32
See application file for complete search history.

(56) References Cited

U.S. PATENT DOCUMENTS

2008/0069873 A1* 3/2008 Pearnchob ........... A61K 9/5073
424/459

OTHER PUBLICATIONS

Thakral et al, Eudragit S-100 entrapped chitosan microspheres of valdecoxib for colon cancer, 2010, J Mater Sci: Mater Med, 21, pp. 2691-2699.*

Amos Cahan; "SCFA Colonic Composition"; U.S. Appl. No. 14/963,521, filed Dec. 9, 2015.

List of IBM or Patent Applications Treated as Related; Date Filed: Jun. 2, 2016, pp. 1-2.

* cited by examiner

*Primary Examiner* — Trevor Love

(74) *Attorney, Agent, or Firm* — Cantor Colburn LLP; Mercedes Hobson

(57) ABSTRACT

The present invention is directed to a colonic composition including a core having at least one short chain fatty acid selected from the group consisting of butyrate, acetate and propionate, and combinations thereof, or a pharmaceutically acceptable salt or ester thereof; wherein at least one of acetate or propionate is present in the core; and at least one digestion-resistant layer covering the core, the digestion-resistant layer disintegrating in the colon. The present invention is also directed to methods of treatment using the above composition.

3 Claims, No Drawings

SCFA COLONIC COMPOSITION

CROSS-REFERENCE TO RELATED APPLICATIONS

This Application is a Divisional of U.S. patent application Ser. No. 14/963,521 filed Dec. 9, 2015 which is incorporated by reference in its entirety.

BACKGROUND

The present invention is directed to a colonic composition comprising short chain fatty acids (SCFAs), and more specifically to a composition targeting the colon with selected SCFAs, the composition including a core comprising select SCFAs and a digestion-resistant layer covering the core.

There is growing knowledge regarding the beneficial effects of SCFA in the colon. SCFA are naturally formed by colon microorganisms fermenting polysaccharides that are non-digestible by humans. The three main SCFA of interest are acetate, propionate, and butyrate. Acetate acts as a substrate for hepatic de novo lipogenesis via acetyl-coA and fatty acid synthase. Propionate down regulates lipogenesis through inhibition of 3-hydroxy-3-methylglutaryl coenzyme A (HMG-CoA), the rate-limiting enzyme in cholesterol synthesis. Butyrate is an important energy source for colonic mucosa and also controls gene expression through the inhibition of histone deacetylase.

SCFA also regulate gut hormones including peptide YY (PYY) and glucagon-like peptide (GLP), which play a role in secretion of digestive enzymes and satiety. SCFA (especially propionate and butyrate) bind to FFA2 and FFA3 receptors in intestinal L cells.

Orally consumed SCFA are readily absorbed in the small intestine and never reach the colon. Administration of non-digestible carbohydrates such as oligo-fructose can provide SCFA to the colon via microorganism fermentation, but results in the production of all three SCFA to various degrees.

SUMMARY

In one embodiment, the present invention is directed to a colonic composition, comprising a core comprising at least one short chain fatty acid selected from the group consisting of butyrate, acetate and propionate, and combinations thereof, or a pharmaceutically acceptable salt or ester thereof; wherein at least one of acetate or propionate is present in the core; and at least one digestion-resistant layer covering the core, the digestion-resistant layer disintegrating in the colon.

In another embodiment, the present invention is directed to a method of treating a patient suffering from a weight loss disorder, a condition that benefits from reduction of cholesterol, a condition of the colon, or diabetes or increased risk for developing diabetes, the method comprising administering to the patient a dosage form containing a therapeutically effective amount of the colonic composition of the invention.

DETAILED DESCRIPTION

As indicated above, the present invention is directed to colonic compositions and related methods that utilize short chain fatty acids (SCFAs) and their derivatives to provide health benefits or treatment of diseases or conditions in the colon. In one embodiment, the composition of the invention includes a core comprising at least one short chain fatty acid selected from the group consisting of butyrate, acetate and propionate, and combinations thereof, or a salt or ester thereof, wherein at least one of acetate or propionate is present in the core; and at least one digestion-resistant layer covering the core, wherein the digestion-resistant layer disintegrates in the colon. Each of these components is discussed in more detail below.

The colonic composition of the present invention comprises a core containing at least one SCFA selected from butyrate, acetate or propionate. Each of these SCFAs may take any suitable chemical form which may be advantageously selected for therapeutic or compositional purposes, for example, acid form, salt form, ester form, and the like. According to the invention, the core may include each of the SCFAs individually or in any combination, however at least either acetate or propionate must be included in the core formulation.

In some embodiments the at least one SCFA can be present as a pharmaceutically acceptable salt. "Pharmaceutically acceptable salts" as defined herein include derivatives of the disclosed SCFA compounds wherein the parent compound is modified by making non-toxic salts of the carboxylate group thereof, and further refers to pharmaceutically acceptable hydrates, solvates of such compounds, and such salts. Examples of pharmaceutically acceptable salts include, but are not limited to, mineral or organic acid salts of the carboxylic acid group of the SCFA. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in *Remington's Pharmaceutical Sciences*, 17th ed., Mack Publishing Company, Easton, Pa., p. 1418 (1985). In some embodiments the SCFA can be present as an ester of the SCFA's carboxylic acid with a branched or unbranched alkyl alcohol of one to 6 carbons. For example, the SCFA can be present as an ethyl ester, propyl ester, butyl ester, isopropyl ester, t-butyl ester, pentyl ester, or hexyl ester.

In some embodiments, the core may comprise additional SCFA other than acetate, propionate or butyrate. Additional SCFAs useful in the invention include, for example, alkyl monocarboxylic acids, straight chain or branched, of from two to six carbons. Examples of additional SCFA include isobutyrate, t-butyl carboxylate, pentanoate, hexanoate, and the like. The additional SCFA may be an SCFA substituted with one to three substituents such as halogen (fluoro, chloro, bromo, iodo), cyano, hydroxy, methoxy, keto, and the like. For example, substituted SCFAs useful as additional SCFAs include hydroxyacetate, ketopropionate, 4,4,4-trifluorobutyrate, and the like.

The core may additionally comprise a pharmaceutically acceptable carrier. Carriers suitable for use in the core component of the invention include excipients and diluents, and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorings, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active and/or inactive agents may be included in the pharmaceutical compositions, provided that such agents do not substantially interfere with the activity of the SCFA and related compounds used in the pharmaceutical compositions.

The colonic composition of the invention includes a digestion-resistant layer covering the core. "Digestion-resistant layer" as used herein means that a layer is resistant to digestion or degradation in the proximal parts of the gastrointestinal tract (namely mouth, esophagus, stomach and the first two parts of the small intestine) but is degraded in the colon. In a typical digestive process for a human subject, "digestion resistant layer" can mean that the layer remains at least 50%, at least 75% or preferably at least 90% intact at the time a composition comprising the layer reaches the colon. The digestion-resistant layer is preferably made of at least one layer of biocompatible natural or man-made polymer which. The digestion-resistant layer is designed to release SCFA core within the lumen of the colon. Disintegration of the digestion-resistant layer may be mediated by environmental factors such as a basic pH or digestion by the colon microbiome. It may also occur in a time-dependent manner and designed to occur within hours to days after ingestion. Remnants of the digestion-resistant layer that are not absorbed through the colon mucosa are designed to be excreted in feces of the user.

Examples of useful materials that may comprise the digestion-resistant layer include eudragit, hydroxymethylcellulose, chitosan, pectin, guar gum, chondroitin sulfate, amylose, alginate, and the like, and combinations thereof. In some embodiments, at least one digestion resistant layer comprises eudragit, and in some embodiments at least one digestion-resistant layer comprises hydroxymethylcellulose.

In some embodiments the core may comprise one selected SCFA or a combination of SCFAs. Useful ranges of each of the selected SCFAs range from 0 wt % to 100 wt %, based on the total weight of the SCFAs. For example, the combination of SCFAs can be 50 wt % acetate and 50 wt % butyrate, or 10 wt % acetate and 90 wt % butyrate, or 60 wt % propionate and 40 wt % butyrate, based on the total weight of SCFA, among other acceptable combinations. The selected ratios and weight percents of the SCFA compounds in the invention can be easily determined and selected by one of skill in the art based on the appropriate application.

The weight ratio of the total weight of SCFA to the total weight of the core may be from 1:50 to 1:10, from 1:10 to 1:5, from 1:5 to 1:2, or from 1:2 to 1:1.

The weight ratio of the core to the digestion-resistant layer may be from 1:10 to 20:1, from 1:10 to 10:1, from 1:5 to 5:1, or from 1:2 to 2:1.

The colonic composition of the invention is preferably formulated as unit doses for ease of administration. The amount of SCFA in a unit dose may be generally varied or adjusted from about 1.0 milligram to about 100 milligrams, from about 10 to about 1000 milligrams, or from about 1000 to about 3000 milligrams, according to the particular application and the potency of the compound. A unit dose may be administered to a patient 1, 2, or 3 or more times per day, depending on the dose required for effective treatment. The actual dosage employed may be varied depending upon the patient's age, sex, weight and severity of the condition being treated. The amount of a unit dose may be based on mg of SCFA per kg of the patient's body weight, or mg/kg. The unit dose for a patient can be from about 0.1 mg/kg to about 10 mg/kg, from about 1 to about 10 mg/kg, or from about 10 to about 100 mg/kg.

In another embodiment, the dosage form is a tablet, a capsule, or a liquid form.

In another embodiment, treating the patient with the dosage form comprises providing the dose to the patient through the mouth, a feeding tube, an enterostomy, or per rectum.

In some embodiments of the invention, a colonic composition containing SCFA is ingested by mouth, swallowed and passes through the stomach where it remains undigested. The colonic composition then proceeds along the small intestine where it is not absorbed. When the colonic composition reaches the colon, it loses its digestion-resistant layer and becomes an uncoated core which interacts with the colon content and the colon wall (mucosa). SCFA that comprise the core can be absorbed through the colon wall (mucosa).

The composition of the invention is useful for treating patients suffering from conditions of the colon or conditions benefitting from receiving SCFA through the colon. The invention includes a method of treating a patient suffering from a weight loss disorder, a condition that benefits from reduction of cholesterol, a condition of the colon, or diabetes or increased risk of developing diabetes, comprises administering to the patient a dosage form containing a therapeutically effective amount of the above-described colonic composition.

The term "therapeutically effective amount" of a compound of the colonic composition of the present invention is defined herein to mean an amount effective, when administered to a human or non-human patient, to provide a therapeutic benefit such as an amelioration of symptoms, e.g., an amount effective to decrease the symptoms of a weight loss disorder, symptoms of a disorder that benefits from reduction of cholesterol, or symptoms of a disorder associated with a condition of the colon, and including an amount sufficient to reduce the above mentioned symptoms. In certain circumstances a patient suffering from the above described disorders may not present symptoms. Thus a therapeutically effective amount of a compound is also an amount sufficient significantly reduce the detectable level of appropriate biomarkers in the patient's blood, serum, other bodily fluids, or tissues. For example, a therapeutically effective amount to treat a disorder that benefits from reduction of cholesterol can be an amount sufficient to significantly reduce blood LDL cholesterol. The invention also includes, in certain embodiments, using compounds of the colonic composition of the present invention in prophylactic treatment and therapeutic treatment. In the context of prophylactic or preventative treatment a "therapeutically effective amount" is an amount sufficient to significantly decrease the treated patient's risk of suffering from the above described disorders. For example, prophylactic treatment may be administered when a subject will knowingly be exposed to treatment that is associated with a risk of weight loss, such as major surgery. A significant reduction is any detectable negative change that is statistically significant in a standard parametric test of statistical significance such as Student's T-test, where p<0.05.

In one embodiment a patient suffering from a weight loss disorder can be treated with the colonic composition of the present invention preferably comprising acetate. Acetate is believed to up-regulate lipogenesis. This approach can be used as part of a refeeding or anabolic program in patients with anorexia nervosa or those following prolonged hospitalization, chemotherapy, major surgery, or chronic disease. This approach can be used in patients with cachexia (weight loss) due to chronic disease such as malignancy, rheumatologic disease or heart failure. The weight loss disorder can further include disorders that are expected to lead to weight loss, such as malnutrition or a catabolic state, even if actual weight loss has not yet occurred.

In another embodiment a patient suffering from a condition that benefits from reduction of cholesterol can be treated with the colonic composition of the present invention preferably comprising propionate. Cholesterol is associated with atherosclerosis including coronary artery disease, cerebrovascular disease, renal artery disease and peripheral vascular disease. It is well established that lower levels of low density lipoproteins (LDL cholesterol) are associated with reduced cardiovascular risk. Moreover, it is established that reducing LDL cholesterol levels by drugs inhibiting the rate-limiting enzyme in cholesterol synthesis, HMG CoA-Reductase reduces cardiovascular morbidity and mortality. Without being bound by theory, it is believed that propionate inhibits HMG CoA-Reductase and may be accountable for some of the health benefits associated with fiber consumption. A colonic composition of the present invention containing propionate or other SCFA with similar effects can be used to inhibit cholesterol synthesis and to control cardiovascular risks. One clinical benefit associated with their use is the fact they do not affect the absorption of other drugs, as they are only released to the gastrointestinal lumen distal to where most other drugs are absorbed. In some embodiments the patient is suffering from high cholesterol, and in other embodiments the patient has normal cholesterol but suffers from a condition that benefits from reduction of cholesterol to below normal levels (such as cardiovascular disease). As lower cholesterol lowers risk of cardiac events even for healthy individuals with normal cholesterol levels, in some embodiments treating a patient suffering from a condition that benefits from reduction of cholesterol can include treating a healthy person with normal cholesterol, in order to gain the benefits of cholesterol lowering.

In one embodiment, a patient suffering from a condition of the colon can be treated with the colonic composition of the present invention preferably comprising butyrate. Butyrate is an important source of energy for the colon mucosa and can provide up to 10% of the total energy demand of the body. Some clinical conditions are associated with increased energy demand of the colon mucosa or with reduced energy supply to the colon mucosa. Some clinical conditions are associated with increased body energy demand or decreased body energy supply. The current invention may be used to treat any or all of the aforementioned condition categories. In some embodiments, the patient is suffering from a condition of the colon, including ischemic colitis, inflammatory bowel disease, colitis from radiation or chemotherapy, typhlitis, or colon cancer.

For example, ischemic colitis is a state of inadequately low blood supply to the colon or a portion of it. It usually results from acute or chronic conditions affecting the mesenteric arteries or veins such as atherosclerosis, infarction, embolus, thrombus. Colonic ischemia may result from increased venous pressure in the mesenteric or systemic venous system due to right heart failure or portal hypertension. This group of diverse clinical conditions may result in abdominal pain, reduced appetite, impaired peristalsis but also in mucosal damage that is associated with bacterial translocation across it and sepsis or peritonitis. Direct energy supply to the colon mucosa in the form of SCFA preferably including butyrate may compensate for the inadequate supply of nutrients to the colonic mucosa through the blood and help maintain the function of the colonic mucosa, including water absorption and protection against bacterial translocation.

Patients following major surgery, especially abdominal surgery, cannot consume food for a period of time that commonly extends to days because of reduced consciousness, ileus and suspected or diagnosed leaking anastomoses. Some patients have decreased appetite and consume fewer calories than their needs. Other severely ill patients are fed through total parenteral nutrition but can still swallow pills or receive pills through a feeding tube or an enterostomy. These patients commonly do not receive the full amount of nutrients and calories they need, and using the colonic composition of the present invention can both maintain the wellness of their colon mucosa and increase their caloric intake.

The turnover rate of cells in the colonic mucosa is high, resulting in high metabolic needs. It also accounts for the colon mucosa susceptibility to being damaged by radiation therapy and chemotherapy, which are at times intended to treat cancer elsewhere but cause damage to the colon as an adverse effect. Colitis from radiation or chemotherapy may result in severe pain, diarrhea and inflammation. Damage to the mucosal barrier may lead to bacterial translocation and sepsis. When chemotherapy-induced neutropenia is present, the mucosal barrier is further compromised, potentially resulting in severe inflammation around the colon (typhlitis) and in an increased risk of bacteremia. In fact, most of the cases of bacteremia or fungemia in neutropenic patients are the result of translocation of microorganisms across the colon mucosa.

In one embodiment, treatment of a patient with the colonic composition of the present invention preferably comprising butyrate, can provide the energy needed for the colon mucosa to regenerate faster following radiation or chemotherapy injury. It may thus reduce the risk of disseminated infection as a result of microbial translocation across the colon mucosa.

In another embodiment, treatment of a patient using the colonic composition of the present invention preferably comprising butyrate can be used wherein the condition of the colon is associated with higher metabolic needs of the colon mucosa such as inflammatory bowel disease (e.g. Crohn's disease or ulcerative colitis) or graft versus host disease involving the colon.

In another embodiment, treatment of a patient using the colonic composition of the present invention preferably comprising butyrate can be used wherein the condition of the colon is associated with resection of the gallbladder, wherein SCFA are formed in the colon to a lesser extent in those patients because of reduced concentration of bile salts reaching the colon. The colonic composition of the present invention preferably comprising butyrate can also be used to provide energy to the colon mucosa, especially when blood supply is compromised (e.g. ischemic colitis, heart failure) or the metabolic needs are increased (e.g. after chemotherapy or radiation therapy). In this context, it may prevent or alleviate radiation colitis and typhlitis.

It has been suggested that at least part of the therapeutic effect of metformin (a drug used in the prevention and treatment of diabetes) is mediated by alteration of SCFA production in the colon, more specifically alteration of butyrate levels in the colon. In one embodiment, treatment of a patient using the colonic composition of the present invention preferably comprising butyrate can be used to improve glycemic control when a patient has diabetes or is at risk of developing diabetes.

In another embodiment, the core comprises propionate.

In another embodiment, the core comprises acetate

In another embodiment, the at least one digestion resistant layer comprises eudragit.

In another embodiment the at least one digestion resistant layer comprises hydroxymethylcellulose.

In another embodiment the at least one digestion resistant layer comprises a composition selected from the group consisting of Chitosan, pectin, guar gum, chondroitin sulfate, amylose, alginate, and combinations thereof.

In another embodiment, a colonic composition includes any or all of the naturally occurring SCFA formed within the human colon, namely propionate, butyrate or acetate, and includes at least one of propionate or acetate.

In another embodiment, a colonic composition may include at least one naturally occurring SCFA that is not normally found within the human colon.

In yet another embodiment, the colonic composition may include at least one artificially synthesized SCFA which has therapeutic effects on the human body.

In another embodiment, the patient is suffering from a weight loss disorder.

In another embodiment, the weight loss disorder is anorexia nervosa, malnutrition, or weight loss following prolonged hospitalization, chemotherapy, major surgery, or chronic disease.

In another embodiment, the weight loss disorder is anorexia nervosa.

In another embodiment, the at least one short chain fatty acid comprises acetate.

In another embodiment, the patient is suffering from a condition that benefits from reduction of cholesterol.

In another embodiment, the patient is suffering from high cholesterol.

In another embodiment, the patient has normal cholesterol, but suffers from a condition that benefits from reduction of cholesterol to below normal levels.

In another embodiment, the condition is a cardiovascular disease.

In another embodiment, the at least one short chain fatty acid comprises propionate.

In another embodiment, the patient is suffering from diabetes or increased risk of diabetes, or from a condition of the colon, including ischemic colitis, inflammatory bowel disease, colitis from radiation or chemotherapy, typhlitis, or colon cancer.

In another embodiment, the at least one short chain fatty acid comprises butyrate.

Unless otherwise specified, all % values herein are weight % (wt %), based on the total weight of the colonic composition.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A colonic composition, consisting of:
   a core consisting of at least one short chain fatty acid selected from the group consisting of butyrate, acetate and propionate, and combinations thereof, or a pharmaceutically acceptable salt or ester thereof; wherein at least one of acetate or propionate is present in said core; and
   at least one digestion-resistant layer covering said core, said digestion-resistant layer disintegrating in the colon.

2. The colonic composition of claim 1, wherein said core comprises acetate.

3. The colonic composition of claim 1, wherein said at least one digestion resistant layer comprises at least one material selected from the group consisting of hydroxymethylcellulose, chitosan, pectin, guar gum, chondroitin sulfate, amylose, alginate, and combinations thereof.

* * * * *